United States Patent

Solesbee et al.

[11] Patent Number: 5,485,837
[45] Date of Patent: Jan. 23, 1996

[54] STRAP FOR COMBINING TRACHEOTOMY TUBE AND MOIST AIR MASK

[76] Inventors: Angela M. Solesbee; Irene D. Hebert, both of 6 Bethany Woods Dr., Asheville, N.C. 28805

[21] Appl. No.: 157,388

[22] Filed: Nov. 23, 1993

[51] Int. Cl.[6] ............................ A61M 16/00; A62B 9/06
[52] U.S. Cl. ................ 128/207.17; 128/207.14; 128/DIG. 26; 128/DIG. 15; 128/200.26
[58] Field of Search ................. 128/200.26, 201.13, 128/207.14, 207.17, 911, 912, DIG. 26, 206.21, 206.27, DIG. 15, DIG. 23, 207.11; 604/268, 303, 308, 332, 337, 345

[56] References Cited

U.S. PATENT DOCUMENTS

| | | | |
|---|---|---|---|
| 3,236,236 | 2/1966 | Hudson | 128/207.17 |
| 3,585,997 | 6/1971 | Ancerewicz, Jr. | 604/345 |
| 3,773,048 | 11/1973 | Kirkliauskas | 604/345 |
| 3,824,999 | 7/1974 | King | 128/207.17 |
| 3,927,676 | 12/1975 | Schultz | 128/207.17 |
| 4,313,437 | 2/1982 | Martin | 128/207.17 |
| 4,326,515 | 4/1982 | Shaffer | 128/207.17 |
| 4,331,144 | 5/1982 | Wapner | 128/DIG. 26 |
| 4,367,735 | 1/1983 | Dali | 128/207.17 |
| 4,520,813 | 6/1985 | Young | 128/207.17 |
| 5,026,362 | 6/1991 | Willett | 604/345 |
| 5,027,811 | 7/1991 | Tuxill | 128/207.17 |
| 5,101,822 | 4/1992 | Kimmel | 128/207.17 |
| 5,146,913 | 9/1992 | Khorsandian et al. | 128/207.17 |
| 5,338,315 | 8/1994 | Baker | 604/345 |
| 5,357,952 | 10/1994 | Schuster et al. | 128/912 |

*Primary Examiner*—Kimberly L. Asher
*Attorney, Agent, or Firm*—Carter & Schnedler

[57] ABSTRACT

There is provided a strap used to combine a tracheotomy tube and moist air mask into a unitary apparatus. The apparatus includes a single soft cushioned strap connected to a tracheotomy tube base and to a moist air mask. The moist air mask covers the tracheotomy tube base. The apparatus eliminates the need for a separate elastic band for the mask and provides comfort for the patient and is easier to use.

1 Claim, 2 Drawing Sheets

STRAP FOR COMBINING TRACHEOTOMY TUBE AND MOIST AIR MASK

BACKGROUND OF THE INVENTION

This invention relates to apparatus utilized in post-tracheotomy procedures. More particularly it relates to tracheotomy tubes and moist air plenum masks.

Tracheotomy is a common surgical procedure. An opening is made into the trachea and an indwelling device called a tracheotomy tube is inserted. This allows for bypass of an upper airway obstruction, removal of tracheobronchial secretions, permitting the use of mechanical ventilation, preventing aspiration of oral or gastric secretions into the trachea in the unconscious or paralyzed patient and replacing an endotracheal tube. The tracheotomy tube itself is normally integral with a base plate having a hole therethrough for receiving the tube. The base plate is made to be flush against the outside of a patient's neck.

Various means for holding the tracheotomy tube in place have been devised over the years, including the use of adhesive tape as well as a thin elastic strap. U.S. Pat. No. 4,331,114 issued to Wapner teaches a substantial improvement for securing a tracheotomy tube in position on a patient. The Wapner patent teaches the use of first and second straps made of soft sponge-like materials forming a soft band surrounding the patient's neck which is both comfortable to the patient and easy to adjust due to the placement of VELCRO on the outside surface of the first strap and on the inside surface of the second strap. The band is secured to the tracheotomy tube base plate by a pair of strips extending through a pair of open slots in the base plate.

When using a tracheotomy tube, the normal moistening facilities of the patient's nasal passages are bypassed, resulting in substantially dry air being breathed by the patient. This problem is exacerbated in hospitals and nursing facilities where there is air conditioning and the humidity is already low. Therefore, it is common practice to supply the tracheotomy patient with moist air to the outside opening of the tracheotomy tube.

The application of moist air is normally accomplished through a tracheotomy mask which is received over the tracheotomy tube holder. An example of such tracheotomy mask is shown in U.S. Pat. No. 3,236,236 issued to Hudson. The Hudson patent shows a tracheotomy mask connected to a source of moist air. The mask acts as a plenum and covers the tracheotomy tube holder. The mask is separately held in place on the front of the patient's neck by a thin elastic band which contacts the back of the neck.

Thus, in situations where moist air is added to the patient, it is common practice to use a tracheotomy tube holder such as shown in the Wapner patent and a separate tracheotomy mask as shown in the Hudson patent. This results in two separate straps around the patient's neck, one of which is thin and irritating to the patient.

The care of tracheotomy patients by nurses in hospitals and nursing facilities requires substantial time and effort. It is common for the tracheotomy tube to be adjusted at regular intervals such as every two to four hours, or as needed. This requires the removal of the moist air mask. To apply and to remove the tracheotomy mask, the nurse must lift the patient's head in order to apply or remove the elastic band around the patient's neck. This exposes the nurse to the patient's bodily fluids and is further disruptive to the patient. In addition, the elastic band often becomes entangled with the patient's hair. Furthermore, because the elastic band is thin, it can leave marks on the patient's neck and cause general discomfort to the patient and, in some cases, skin damage.

OBJECTS OF THE INVENTION

It is therefore one object of this invention to provide an improved apparatus for use with a tracheotomy tube and moist air mask.

It is another object to provide an improved apparatus for use with a tracheotomy tube and moist air mask which is more convenient and safer for the nurse to use and is more comfortable to the patient.

It is still another object to provide a combined tracheotomy tube and moist air mask apparatus which is inexpensive to produce.

SUMMARY OF THE INVENTION

In accordance with one form of this invention, there is provided a tracheotomy apparatus for use with a tracheotomy tube base including a moist air mask and an elongated strap. The mask has an opening for receiving moist air. The elongated strap encircles at least a portion of the neck of the patient. The strap includes first and second ends. The strap is connectable to the mask and to the base such that the mask and the base may be held in position at the front of the neck of the patient by the strap, thereby eliminating the need for separate straps for the mask and for the tube base.

It is preferred that the strap be made primarily of a soft sponge-like material to provide substantial comfort to the patient. It is also preferred that the strap include a main strap and a moveable extension member so that the length of the strap is adjustable. In addition, it is preferred that the tracheotomy tube base be connected to the ends of the strap while the mask be connected along the sides of the strap.

BRIEF DESCRIPTION OF THE DRAWINGS

The subject matter which is regarded as the invention is set forth in the claims. The invention itself, however, together with further objects and advantages thereof may be better understood by reference to the following description taken in conjunction with the accompanying drawings in which:

DESCRIPTION OF THE PREFERRED EMBODIMENTS

Figure 1:
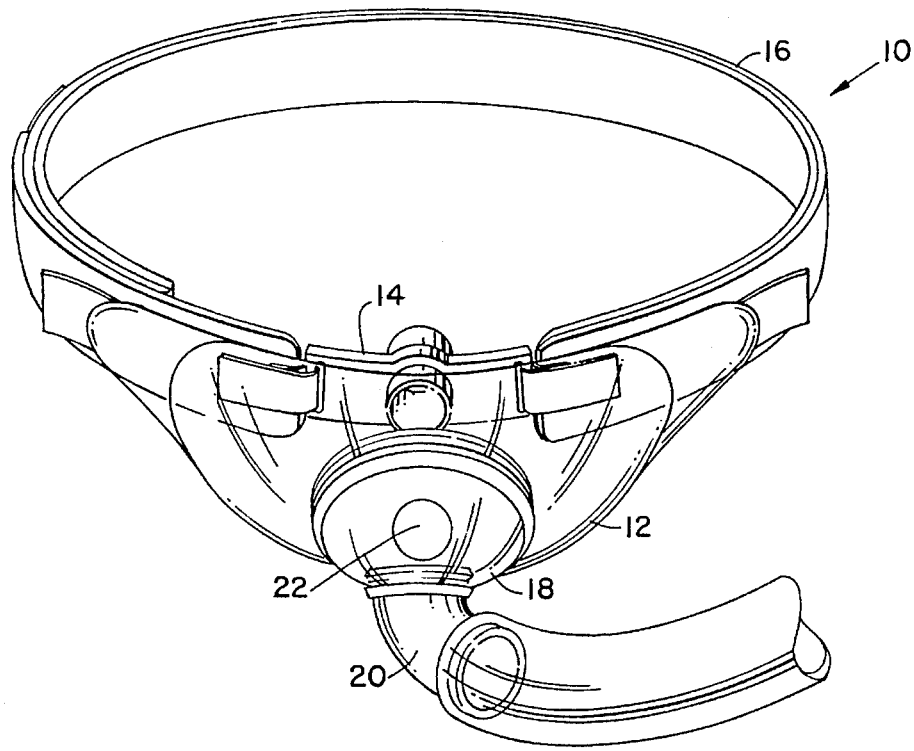
FIG. 1 is a simplified pictorial view of the tracheotomy tube and moist air mask of the subject invention showing portions thereof in phantom.
Figure 2:
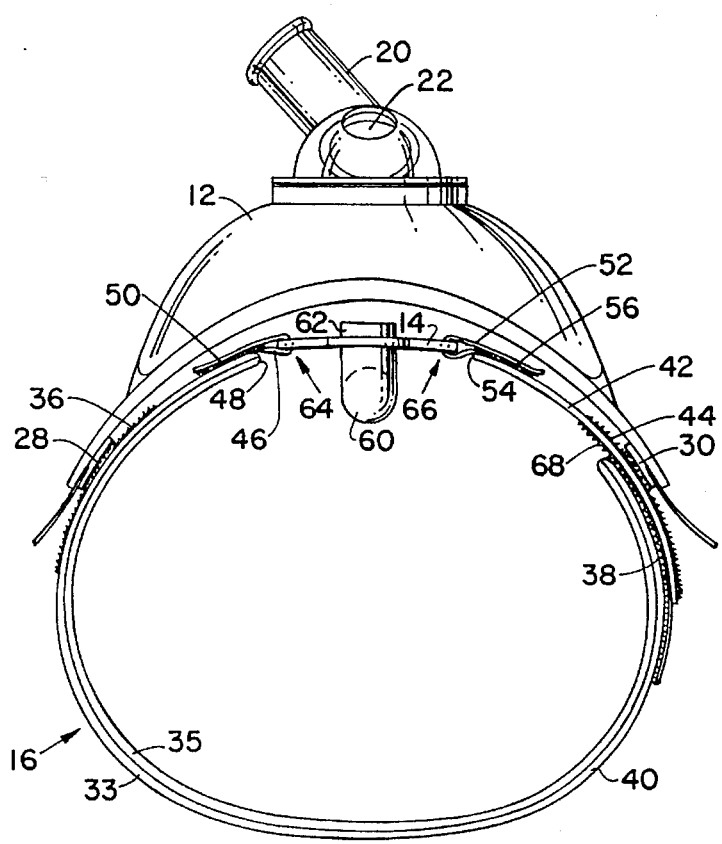
FIG. 2 is a top view of the apparatus of FIG. 1.
Figure 3:
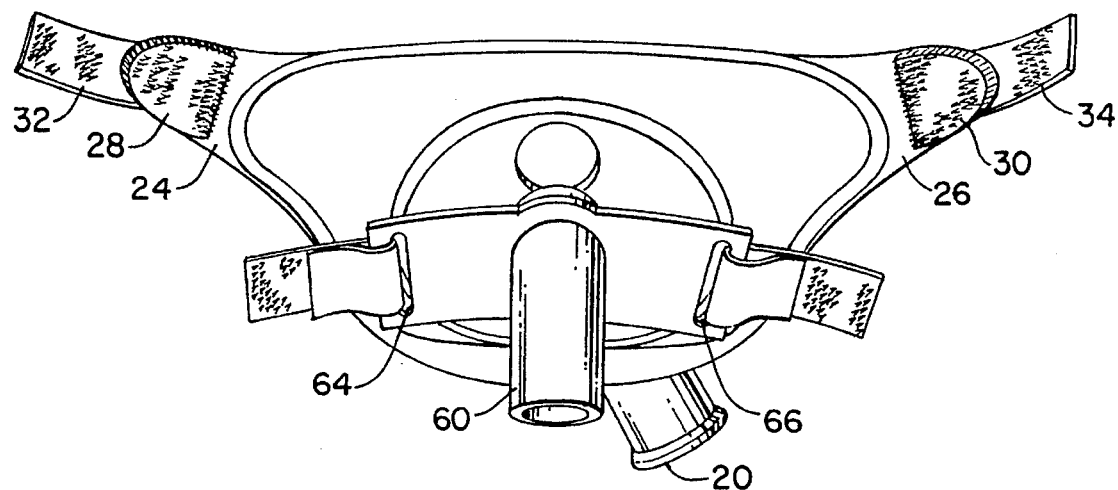
FIG. 3 is a rear elevational view showing portions of the mask and tracheotomy tube holder of FIG. 1 with the strap being removed for clarity.
Figure 5:
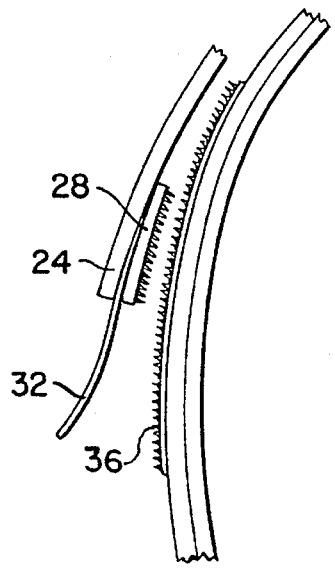
FIG. 5 is a partial top view of a portion of the opposite of FIG. 2 showing the other side of the strap connected to the other side of the mask in more detail.

Referring now more particularly to FIGS. 1 through 5, there is provided a tracheotomy apparatus 10, including moist air mask 12, tracheotomy tube base 14 and strap 16.

Mask 12 is preferably made of a soft pliable plastic material such as polyethylene and is molded to fit snugly about the front of the neck of the patient. Mask 12 includes hemispherical adaptor 18 to which is attached moist air connector tube 20. Tube 20 is adapted to be connected to a source of moist air (not shown). Adaptor 18 has a hole 22 therein through which the exhalent of the patient flows. It is preferable that the hemispherical adaptor 18 be made of a harder plastic then the remainder of the mask 12.

Mask 12 includes a pair of ear-like projections 24 and 26. A first connector member in the form of VELCRO fastener 28 is glued to ear 24 and a second connector member 30 in the form of another VELCRO fastener is glued to ear 26. Tab 32 extends from ear 24 and is received between ear 24 and VELCRO fastener 28 and is secured thereto by the glue. Likewise, tab 34 is received between ear 26 and VELCRO fastener 30 and is secured thereto by the glue. Tabs 32 and 34 enable the nurse to more easily remove the mask 12 from strap 16, as will be explained below.

Strap 16 is preferably made of two plies 33 and 35. Each ply 32 and 34 is primarily made of soft foam rubber material with outer backing made of a material to which human skin is not normally sensitive such as, for example, cotton. This two-ply soft material presents a very comfortable feel to the patient. Strap 16 includes a VELCRO fastener 36 in forming a seventh connection member. VELCRO fastener 36 is adapted to be interconnected with Velcro fastener 28 which is attached to the mask. Strap 16 further includes VELCRO sensitive cloth 38 in the form of an eighth connector member. Strap 16 is preferably formed by two separate straps, namely, main two-ply strap 40 and extension member 42 to provide adjustability to the length of strap 16.

Extension member 42 includes VELCRO fastener 44 on one side thereof and Velcro fastener 46 on the opposing side thereof. VELCRO fastener 46 is adapted to intermate with VELCRO sensitive cloth 38 on the main strap 40. VELCRO fastener 44 is adapted to intermate with VELCRO fastener 30 which is attached to mask 12.

Main strap 40 includes strip 46 forming a fifth connector member extending from the end 48 thereof. Strip 46 also includes a VELCRO fastener 50. Extension strap 42 includes a strip 52 forming a sixth connector member extending from the end 54 thereof, and further includes VELCRO fastener 56. Preferably, strips 46 and 52 are sown to the respective primary strap and extension strap so that they are firmly secured thereto. Strips 46 and 52 are used to hold tracheotomy tube base 14, and thus tracheotomy tube 60 firmly in place at the tracheotomy opening in the patient's neck. Tracheotomy tube 60 extends into the opening in the patient's neck while the tube 62 extends into the inside of the mask 12 for receiving moist air from tube 20.

Tracheotomy tube base 14 includes third and fourth connector members in the form of a pair of slotted openings 64 and 66 through which strips 46 and 52 are respectively received. Strips 46 and 52 are looped and are respectively attached to the main strap 40 by the VELCRO fastener 50 and to the extension strap 42 by Velcro fastener 56. The length of the strips 46 and 52 also provide a degree of adjustability to the overall circumference of strap 16 to accommodate patients having various neck circumferences.

Figure 4:
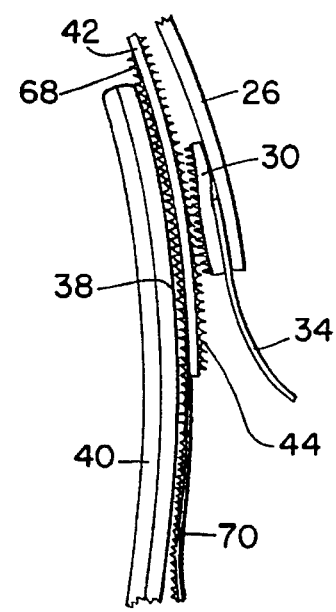
FIG. 4 is a partial top view of a portion of the apparatus of FIG. 2 showing the one side of the strap connected to the mask in more detail.

As can be seen from FIG. 4, extension strap 42 includes VELCRO fastener 68 for attaching the extension strap to main strap 40. Release tab 70, which is made of a finer VELCRO, enables one to more easily remove the extension strap 42 from main strap 40. The relationship between the extension strap 42 and main strap 40 through those VELCRO fasteners enable the overall length of strap 16 to be made adjustable.

A procedure using the above described apparatus is set forth below. A patient that has just had a procedure known as a tracheotomy is returned to the hospital room. The tracheotomy tube 60 is usually held in place with a form of twill tape for stability until a better apparatus can be utilized.

First, one gathers the following supplies that will be needed to do the appropriate changes:

A. a suture removal kit which includes a pair of sterile scissors and tweezers;

B. a tracheotomy tube holder or strap 16;

C. a tracheotomy mask 12 which is adaptable to the holder;

D. a pair of sterile gloves;

E. two packs of 4×4 sterile gauze; and

F. a bottle of sterile saline.

The nurse then completes the following procedures:

A. prepare a sterile field so not to introduce any bacterial agents into the surgical field;

B. open all of the supplies using sterile technique;

C. moisten one of the 4×4 gauze with the sterile saline and leave the other dry;

D. apply sterile gloves;

E. take the scissors and cut the twill tape that is securing the tracheotomy tube 60; note, you must keep one hand on the tracheotomy tube at all times after removing the securing apparatus to prevent the tube from being coughed out;

F. use the moist 4×4 gauze to clean gently around the tracheotomy opening;

G. use the dry 4×4 gauze to carefully dry the area;

H. place the strips 50 and 52 of the tracheotomy tube strap 16 through the openings 64 and 66 in tracheotomy tube base 14;

I. lift the patient's neck slightly to wrap the other end of two-ply strap 40 around the back of the neck;

J. use the Velcro attachments 38 and 46 on the tracheotomy tube strap 16 to adjust for proper neck size;

K. cut off the excess material from two-ply strap 40 and discard it; and

L. place the mask in front of the tracheotomy tube and attach VELCRO fasteners 28 and 30 to the VELCRO fasteners 36 and 44 on the tracheotomy tube strap 16 allowing for proper fit and comfort for the patient.

Thus, there is provided an apparatus for holding a tracheotomy tube and moist air mask in place on a patient utilizing a single adjustable and comfortable padded strap thereby eliminating the nuisance and hazards associated with the prior art elastic band which was heretofore used to secure the mask in place about the patient's neck.

Having described the preferred embodiment of the invention in detail, those skilled in the art will appreciate that modifications may be made in the invention without departing from its true spirit and scope. Therefore, it is not intended that the scope of this invention be limited to this specific embodiment illustrated and described. Rather, it is intended that the scope of the invention be determined by the appending claims and their equivalences.

What is claimed is:

1. A tracheotomy tube and moist air mask combination comprising a base plate, and a strap arrangement wherein said strap arrangement is adapted to extend about the neck of a patient and having two ends, said base plate being connected between said two ends of said strap arrangement, said base plate having a central hole that receives said tracheotomy tube that extends out of a patient's trachea, said combination further comprising means for permitting attachment and removal of said moist air mask to said strap arrangement without removal of said strap arrangement or disconnection of said base plate from either said strap arrangement or said tracheotomy tube, said means comprising a first pair of connection members disposed on said strap arrangement on opposing sides of said base plate, and a second pair of connection members on opposing sides of said mask, said first and second pair of connecting members being engageable and disengageable to connect said mask to said single strap arrangement and place said masks over said base plate and tracheotomy tube, and to allow removal of said mask for patient maintenance, respectively.

* * * * *